(12) United States Patent
Geertsen

(10) Patent No.: US 8,900,204 B2
(45) Date of Patent: *Dec. 2, 2014

(54) GEARING MECHANISM FOR AN INJECTION DEVICE

(75) Inventor: Thomas Geertsen, Copenhagen K (DK)

(73) Assignee: Novo Nordisk A/S, Bagsvaerd (DK)

( * ) Notice: Subject to any disclaimer, the term of this patent is extended or adjusted under 35 U.S.C. 154(b) by 145 days.

This patent is subject to a terminal disclaimer.

(21) Appl. No.: 13/528,247

(22) Filed: Jun. 20, 2012

(65) Prior Publication Data

US 2012/0253290 A1    Oct. 4, 2012

Related U.S. Application Data

(63) Continuation of application No. 12/300,540, filed as application No. PCT/EP2007/054796 on May 16, 2007, now Pat. No. 8,226,618.

(60) Provisional application No. 60/813,895, filed on Jun. 15, 2006.

(30) Foreign Application Priority Data

May 16, 2006 (DK) .................................. 2006 00690

(51) Int. Cl.
*A61M 5/00* (2006.01)
*A61M 5/315* (2006.01)

(52) U.S. Cl.
CPC ... *A61M 5/31511* (2013.01); *A61M 2005/3152* (2013.01)
USPC ........................................................ 604/211

(58) Field of Classification Search
USPC .................. 604/207, 208, 211, 223, 224, 228
See application file for complete search history.

(56) References Cited

U.S. PATENT DOCUMENTS

| | | | |
|---|---|---|---|
| 854,399 A | 5/1907 | Bridge |
| 2,392,196 A | 1/1946 | Smith |
| 2,956,563 A | 10/1960 | Sarnoff |
| 3,110,310 A | 11/1963 | Cislak |
| 3,115,135 A | 12/1963 | Sarnoff |
| 3,144,178 A | 8/1964 | Sarnoff et al. |

(Continued)

FOREIGN PATENT DOCUMENTS

| | | |
|---|---|---|
| AU | 2003232576 A1 | 1/2004 |
| CA | 2359375 A1 | 7/2000 |

(Continued)

OTHER PUBLICATIONS

Pearsall, Judy (Editor), Concise Oxford English Dictionary, 2002, Part 10.

(Continued)

*Primary Examiner* — Aarti B Berdichevsky
(74) *Attorney, Agent, or Firm* — Wesley A. Nicolas; Reza Green; Richard W. Bork

(57) ABSTRACT

An injection device comprising: a base member (102); a plunger (104) for driving a piston in a distal direction; a driving member (106); and a gear mechanism (108) providing a gearing between the driving member (106) and the plunger (104) such that then the driving member (106) is moved at a first speed relative to the base member (102), the plunger (104) is moved at a second speed relative to the base member (102); wherein at least two of the base member (102), the plunger (104) and the driving member (106) are pivotally connected to the gear mechanism (108).

17 Claims, 2 Drawing Sheets

(56) References Cited

U.S. PATENT DOCUMENTS

Figure 1:
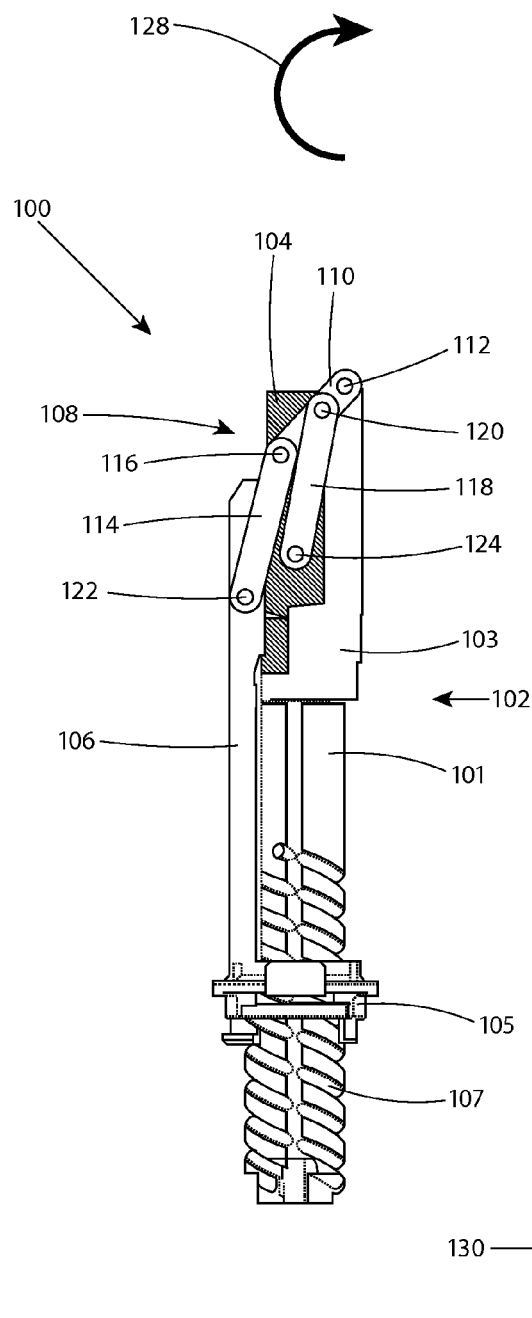

| | | |
|---|---|---|
| 3,556,099 A | 1/1971 | Knight et al. |
| 3,729,003 A | 4/1973 | Hurschman |
| 3,880,162 A | 4/1975 | Simmons |
| 3,944,843 A | 3/1976 | Vaz Martins |
| 4,026,288 A | 5/1977 | Costa et al. |
| 4,231,368 A | 11/1980 | Becker |
| 4,275,727 A | 6/1981 | Keeri-Szanto |
| 4,277,227 A | 7/1981 | Jenkins |
| 4,298,000 A | 11/1981 | Thill et al. |
| 4,300,554 A | 11/1981 | Hessberg et al. |
| 4,313,439 A | 2/1982 | Babb et al. |
| 4,314,556 A | 2/1982 | Ma |
| 4,368,731 A | 1/1983 | Schramm |
| RE31,315 E | 7/1983 | Jenkins et al. |
| 4,393,723 A | 7/1983 | Brand |
| 4,413,760 A | 11/1983 | Paton |
| 4,430,079 A | 2/1984 | Thill et al. |
| 4,465,478 A | 8/1984 | Sabelman et al. |
| 4,470,317 A | 9/1984 | Sabloewski et al. |
| 4,493,704 A | 1/1985 | Beard et al. |
| 4,498,904 A | 2/1985 | Turner et al. |
| 4,515,584 A | 5/1985 | Abe et al. |
| 4,568,335 A | 2/1986 | Updike et al. |
| 4,585,439 A | 4/1986 | Michel |
| 4,634,431 A | 1/1987 | Whitney et al. |
| 4,676,122 A | 6/1987 | Szabo et al. |
| 4,749,109 A | 6/1988 | Kamen |
| 4,812,724 A | 3/1989 | Langer et al. |
| 4,833,379 A | 5/1989 | Kaibel et al. |
| 4,838,860 A | 6/1989 | Groshong et al. |
| 4,865,591 A | 9/1989 | Sams |
| 4,871,351 A | 10/1989 | Feingold |
| 4,883,472 A | 11/1989 | Michel |
| 4,893,291 A | 1/1990 | Bick et al. |
| 4,898,578 A | 2/1990 | Rubalcaba, Jr. |
| 4,919,596 A | 4/1990 | Slate et al. |
| 4,936,833 A | 6/1990 | Sams |
| 4,950,246 A | 8/1990 | Muller |
| 4,973,318 A | 11/1990 | Holm et al. |
| 4,988,337 A | 1/1991 | Ito |
| 4,994,033 A | 2/1991 | Shockey et al. |
| 5,000,744 A | 3/1991 | Hoffman et al. |
| 5,002,537 A | 3/1991 | Hoffman et al. |
| 5,064,098 A | 11/1991 | Hutter, III et al. |
| 5,078,698 A | 1/1992 | Stiehl et al. |
| 5,104,388 A | 4/1992 | Quackenbush |
| 5,112,317 A | 5/1992 | Michel |
| 5,113,869 A | 5/1992 | Nappholz et al. |
| 5,114,406 A | 5/1992 | Gabriel et al. |
| 5,135,485 A | 8/1992 | Cohen et al. |
| 5,163,904 A | 11/1992 | Lampropoulos et al. |
| 5,176,646 A | 1/1993 | Kuroda |
| 5,207,752 A | 5/1993 | Sorenson et al. |
| 5,221,268 A | 6/1993 | Barton et al. |
| 5,226,342 A | 7/1993 | Panin |
| 5,226,895 A | 7/1993 | Harris |
| 5,226,896 A | 7/1993 | Harris |
| 5,244,461 A | 9/1993 | Derlien |
| 5,244,465 A | 9/1993 | Michel |
| 5,246,417 A | 9/1993 | Haak et al. |
| 5,257,987 A | 11/1993 | Athayde et al. |
| 5,271,527 A | 12/1993 | Haber et al. |
| 5,279,585 A | 1/1994 | Balkwill |
| 5,279,586 A | 1/1994 | Balkwill |
| 5,281,198 A | 1/1994 | Haber et al. |
| 5,284,480 A | 2/1994 | Porter et al. |
| 5,292,976 A | 3/1994 | Dessau et al. |
| 5,295,976 A | 3/1994 | Harris |
| 5,304,152 A | 4/1994 | Sams |
| 5,308,340 A | 5/1994 | Harris |
| 5,314,412 A | 5/1994 | Rex |
| 5,318,540 A | 6/1994 | Athayde et al. |
| 5,320,609 A | 6/1994 | Haber et al. |
| 5,331,954 A | 7/1994 | Rex et al. |
| 5,368,572 A | 11/1994 | Shirota |
| 5,370,629 A | 12/1994 | Michel et al. |
| 5,378,233 A | 1/1995 | Haber et al. |
| 5,383,856 A | 1/1995 | Bersin |
| 5,383,865 A | 1/1995 | Michel |
| 5,408,387 A | 4/1995 | Murase et al. |
| 5,440,976 A | 8/1995 | Giuliano et al. |
| 5,445,606 A | 8/1995 | Haak et al. |
| 5,447,150 A | 9/1995 | Bacon |
| 5,478,316 A | 12/1995 | Bitdinger et al. |
| 5,492,534 A | 2/1996 | Athayde et al. |
| 5,496,286 A | 3/1996 | Stiehl et al. |
| 5,505,697 A | 4/1996 | McKinnon, Jr. et al. |
| 5,505,704 A | 4/1996 | Pawelka et al. |
| 5,536,249 A | 7/1996 | Castellano et al. |
| 5,546,932 A | 8/1996 | Galli |
| 5,549,575 A | 8/1996 | Giambattista et al. |
| 5,573,729 A | 11/1996 | Belgardt et al. |
| 5,582,598 A | 12/1996 | Chanoch |
| 5,584,815 A | 12/1996 | Pawelka et al. |
| 5,591,136 A | 1/1997 | Gabriel |
| 5,593,390 A | 1/1997 | Castellano et al. |
| 5,599,314 A | 2/1997 | Neill |
| 5,611,783 A | 3/1997 | Mikkelsen |
| 5,611,784 A | 3/1997 | Barresi et al. |
| 5,626,566 A | 5/1997 | Petersen et al. |
| 5,628,309 A | 5/1997 | Brown |
| 5,637,095 A | 6/1997 | Nason et al. |
| 5,645,052 A | 7/1997 | Kersey |
| 5,662,612 A | 9/1997 | Niehoff |
| 5,674,204 A | 10/1997 | Chanoch |
| 5,679,111 A | 10/1997 | Hjertman et al. |
| 5,681,285 A | 10/1997 | Ford et al. |
| 5,685,864 A | 11/1997 | Shanley et al. |
| 5,688,251 A | 11/1997 | Chanoch |
| 5,709,662 A | 1/1998 | Olive et al. |
| 5,716,990 A | 2/1998 | Bagshawe et al. |
| 5,720,733 A | 2/1998 | Brown |
| 5,725,508 A | 3/1998 | Chanoch |
| 5,728,074 A | 3/1998 | Castellano et al. |
| 5,728,559 A | 3/1998 | Nilsson et al. |
| 5,741,211 A | 4/1998 | Renirie et al. |
| 5,743,889 A | 4/1998 | Sams |
| 5,755,692 A | 5/1998 | Manicom |
| 5,782,633 A | 7/1998 | Muhlbauer |
| 5,807,334 A | 9/1998 | Hodosh et al. |
| 5,807,346 A | 9/1998 | Frezza |
| 5,814,022 A | 9/1998 | Antanavich et al. |
| 5,820,602 A | 10/1998 | Kovelman et al. |
| 5,823,998 A | 10/1998 | Yamagata |
| 5,827,232 A | 10/1998 | Chanoch et al. |
| 5,843,036 A | 12/1998 | Olive et al. |
| 5,879,360 A | 3/1999 | Crankshaw |
| 5,879,630 A | 3/1999 | Lescouzeres et al. |
| 5,882,718 A | 3/1999 | Pommer et al. |
| 5,898,028 A | 4/1999 | Jensen et al. |
| 5,921,966 A | 7/1999 | Bendek et al. |
| 5,928,201 A | 7/1999 | Poulsen et al. |
| 5,933,671 A | 8/1999 | Stephany et al. |
| 5,938,642 A | 8/1999 | Burroughs et al. |
| 5,947,934 A | 9/1999 | Hansen et al. |
| 5,951,530 A | 9/1999 | Steengaard et al. |
| 5,954,689 A | 9/1999 | Poulsen |
| 5,954,700 A | 9/1999 | Kovelman |
| 5,957,889 A | 9/1999 | Poulsen et al. |
| 5,961,496 A | 10/1999 | Nielsen et al. |
| 5,971,963 A | 10/1999 | Choi |
| 5,980,491 A | 11/1999 | Hansen |
| 5,984,900 A | 11/1999 | Mikkelsen |
| 5,989,221 A | 11/1999 | Hjertman |
| 5,998,989 A | 12/1999 | Lohberg |
| 6,003,736 A | 12/1999 | Ljunggren |
| 6,004,297 A | 12/1999 | Steenfeldt-Jensen et al. |
| 6,010,485 A | 1/2000 | Buch-Rasmussen et al. |
| 6,033,376 A | 3/2000 | Rockley |
| 6,033,377 A | 3/2000 | Rasmussen et al. |
| 6,036,675 A | 3/2000 | Thorne et al. |
| 6,048,336 A | 4/2000 | Gabriel |
| 6,074,372 A | 6/2000 | Hansen |
| 6,083,197 A | 7/2000 | Umbaugh |

(56) References Cited

U.S. PATENT DOCUMENTS

| | | |
|---|---|---|
| 6,086,567 A | 7/2000 | Kirchhofer et al. |
| 6,096,010 A | 8/2000 | Walters et al. |
| 6,110,148 A | 8/2000 | Brown et al. |
| 6,110,149 A | 8/2000 | Klitgaard et al. |
| 6,129,080 A | 10/2000 | Pitcher et al. |
| 6,146,361 A | 11/2000 | DiBiasi et al. |
| 6,159,161 A | 12/2000 | Hodosh |
| 6,161,364 A | 12/2000 | Kolberg |
| 6,193,698 B1 | 2/2001 | Kirchhofer et al. |
| 6,221,046 B1 | 4/2001 | Burroughs et al. |
| 6,221,053 B1 | 4/2001 | Walters et al. |
| 6,231,540 B1 | 5/2001 | Smedegaard |
| 6,235,004 B1 | 5/2001 | Steenfeldt-Jensen et al. |
| 6,245,046 B1 | 6/2001 | Sibbitt |
| 6,248,090 B1 | 6/2001 | Jensen et al. |
| 6,248,095 B1 | 6/2001 | Giambattista et al. |
| 6,258,062 B1 | 7/2001 | Thielen et al. |
| 6,268,722 B1 | 7/2001 | Kogure et al. |
| 6,269,340 B1 | 7/2001 | Ford et al. |
| 6,277,097 B1 | 8/2001 | Mikkelsen et al. |
| 6,277,098 B1 | 8/2001 | Klitmose et al. |
| 6,281,225 B1 | 8/2001 | Hearst et al. |
| 6,283,941 B1 | 9/2001 | Schoenfeld et al. |
| 6,287,283 B1 | 9/2001 | Ljunggreen et al. |
| 6,302,869 B1 | 10/2001 | Klitgaard |
| 6,312,413 B1 | 11/2001 | Jensen et al. |
| 6,340,357 B1 | 1/2002 | Poulsen et al. |
| 6,364,860 B1 | 4/2002 | Steck et al. |
| 6,379,339 B1 | 4/2002 | Klitgaard et al. |
| 6,383,167 B2 | 5/2002 | Kirchhofer et al. |
| 6,391,005 B1 | 5/2002 | Lum et al. |
| 6,419,661 B1 | 7/2002 | Kuhr et al. |
| 6,514,230 B1 | 2/2003 | Munk et al. |
| 6,537,251 B2 | 3/2003 | Klitmose |
| 6,537,252 B1 | 3/2003 | Hansen |
| 6,547,755 B1 | 4/2003 | Himbert et al. |
| 6,547,763 B2 | 4/2003 | Steenfeldt-Jensen et al. |
| 6,547,764 B2 | 4/2003 | Larsen et al. |
| 6,562,011 B1 | 5/2003 | Buch-Rasmussen et al. |
| 6,569,126 B1 | 5/2003 | Poulsen et al. |
| 6,582,404 B1 | 6/2003 | Klitgaard et al. |
| 6,585,698 B1 | 7/2003 | Packman et al. |
| 6,599,272 B1 | 7/2003 | Hjertman et al. |
| 6,605,067 B1 | 8/2003 | Larsen |
| 6,613,019 B2 | 9/2003 | Munk |
| 6,663,602 B2 | 12/2003 | Moller |
| 6,666,849 B1 | 12/2003 | Marshall et al. |
| 6,673,033 B1 | 1/2004 | Sciulli et al. |
| 6,692,472 B2 | 2/2004 | Hansen et al. |
| 6,699,224 B2 | 3/2004 | Kirchhofer et al. |
| 6,716,198 B2 | 4/2004 | Larsen |
| 6,726,661 B2 | 4/2004 | Munk et al. |
| 6,752,798 B2 | 6/2004 | McWethy et al. |
| 6,770,288 B2 | 8/2004 | Duirs |
| 6,796,970 B1 | 9/2004 | Klitmose et al. |
| 6,852,404 B2 | 2/2005 | Kuwajima et al. |
| 6,887,238 B2 | 5/2005 | Jahns et al. |
| 6,893,415 B2 | 5/2005 | Madsen et al. |
| 6,899,698 B2 | 5/2005 | Sams |
| 6,899,699 B2 | 5/2005 | Enggaard |
| 6,945,961 B2 | 9/2005 | Miller et al. |
| 7,008,399 B2 | 3/2006 | Larsen et al. |
| 7,080,936 B1 | 7/2006 | Simpson |
| 7,090,662 B2 | 8/2006 | Wimpenny et al. |
| 7,094,221 B2 | 8/2006 | Veasey et al. |
| 7,104,972 B2 | 9/2006 | Moller et al. |
| 7,133,329 B2 | 11/2006 | Skyggebjerg et al. |
| 7,175,055 B2 | 2/2007 | Hansen et al. |
| 7,195,609 B2 | 3/2007 | Huegli |
| 7,195,616 B2 | 3/2007 | Diller et al. |
| 7,241,278 B2 | 7/2007 | Moller |
| 7,500,966 B2 | 3/2009 | Hommann |
| 7,678,084 B2 | 3/2010 | Judson et al. |
| 7,704,238 B2 | 4/2010 | Diller et al. |
| 2001/0016571 A1 | 8/2001 | Ohkubo et al. |
| 2001/0034506 A1 | 10/2001 | Hirschman et al. |
| 2001/0053893 A1 | 12/2001 | Larsen |
| 2002/0002326 A1 | 1/2002 | Causey et al. |
| 2002/0007154 A1 | 1/2002 | Hansen et al. |
| 2002/0020654 A1 | 2/2002 | Eilersen |
| 2002/0049415 A1 | 4/2002 | Fukuda |
| 2002/0052578 A1 | 5/2002 | Moller |
| 2002/0077852 A1 | 6/2002 | Ford et al. |
| 2002/0107486 A1 | 8/2002 | Munk |
| 2002/0120235 A1 | 8/2002 | Enggaard |
| 2002/0165500 A1 | 11/2002 | Bechtold et al. |
| 2002/0173752 A1 | 11/2002 | Polzin |
| 2002/0188250 A1 | 12/2002 | Landau et al. |
| 2003/0009133 A1 | 1/2003 | Ramey |
| 2003/0039679 A1 | 2/2003 | Duirs |
| 2003/0073954 A1 | 4/2003 | Moberg et al. |
| 2003/0114800 A1 | 6/2003 | Veasey et al. |
| 2003/0172924 A1 | 9/2003 | Staniforth et al. |
| 2003/0176871 A1 | 9/2003 | Pavlov et al. |
| 2003/0216663 A1 | 11/2003 | Jersey-Willuhn et al. |
| 2003/0233075 A1 | 12/2003 | Huegli |
| 2004/0010204 A1 | 1/2004 | Weber et al. |
| 2004/0024361 A1 | 2/2004 | Fago et al. |
| 2004/0051368 A1 | 3/2004 | Caputo et al. |
| 2004/0059299 A1 | 3/2004 | Moller |
| 2004/0064109 A1 | 4/2004 | Klint et al. |
| 2004/0097879 A1 | 5/2004 | Woolston |
| 2004/0108339 A1 | 6/2004 | Hansen et al. |
| 2004/0158304 A1 | 8/2004 | Cory et al. |
| 2004/0171983 A1 | 9/2004 | Sparks et al. |
| 2004/0186431 A1 | 9/2004 | Graf et al. |
| 2004/0207385 A1 | 10/2004 | Gafner et al. |
| 2004/0210199 A1 | 10/2004 | Atterbury et al. |
| 2004/0230157 A1 | 11/2004 | Perry et al. |
| 2004/0236282 A1 | 11/2004 | Braithwaite |
| 2004/0249348 A1 | 12/2004 | Wimpenny et al. |
| 2004/0260247 A1 | 12/2004 | Veasey et al. |
| 2004/0267207 A1 | 12/2004 | Veasey et al. |
| 2004/0267208 A1 | 12/2004 | Veasey et al. |
| 2005/0004529 A1 | 1/2005 | Veasey et al. |
| 2005/0019400 A1 | 1/2005 | Deveney et al. |
| 2005/0033244 A1 | 2/2005 | Veasey et al. |
| 2005/0055011 A1 | 3/2005 | Enggaard |
| 2005/0177115 A1 | 8/2005 | Broennimann et al. |
| 2005/0197625 A1 | 9/2005 | Haueter et al. |
| 2005/0205083 A1 | 9/2005 | Staniforth et al. |
| 2005/0268915 A1 | 12/2005 | Wassenaar et al. |
| 2006/0118612 A1 | 6/2006 | Christoffersen et al. |
| 2006/0258988 A1 | 11/2006 | Keitel et al. |
| 2006/0264838 A1 | 11/2006 | Volckmann et al. |
| 2007/0093761 A1 | 4/2007 | Veasey et al. |
| 2007/0244445 A1 | 10/2007 | Moller |
| 2008/0065026 A1 | 3/2008 | Moller |
| 2008/0221530 A1 | 9/2008 | Glejbol et al. |
| 2008/0281275 A1 | 11/2008 | Moller |
| 2009/0043264 A1 | 2/2009 | Glejbol et al. |
| 2009/0062748 A1 | 3/2009 | Moller et al. |

FOREIGN PATENT DOCUMENTS

| | | |
|---|---|---|
| DE | 3048135 A1 | 7/1982 |
| DE | 3236374 A1 | 4/1984 |
| DE | 3609555 A1 | 9/1987 |
| DE | 3638984 A1 | 5/1988 |
| DE | 3923079 A1 | 1/1991 |
| DE | 4223958 A1 | 1/1993 |
| DE | 4419235 A1 | 12/1995 |
| DE | 19503230 A1 | 8/1996 |
| DE | 29513214 U1 | 1/1997 |
| DE | 19723647 C1 | 12/1998 |
| DE | 19838760 A1 | 4/2000 |
| DE | 29907880 U1 | 9/2000 |
| DE | 10103287 A1 | 8/2001 |
| DE | 10201875 C1 | 5/2003 |
| DE | 10229122 A1 | 2/2004 |
| DE | 20317377 U1 | 4/2005 |
| DE | 102004046003 A1 | 3/2006 |
| DK | 200100240 | 11/2001 |
| DK | 2005/00116 U1 | 6/2005 |

(56) References Cited

FOREIGN PATENT DOCUMENTS

| | | |
|---|---|---|
| EP | 15617 | 9/1980 |
| EP | 017318 A1 | 10/1980 |
| EP | 0064858 A1 | 11/1982 |
| EP | 295075 | 12/1988 |
| EP | 327810 A2 | 8/1989 |
| EP | 327910 A2 | 8/1989 |
| EP | 338806 | 10/1989 |
| EP | 0362484 A2 | 4/1990 |
| EP | 387854 | 9/1990 |
| EP | 422482 | 4/1991 |
| EP | 454331 | 10/1991 |
| EP | 498737 | 8/1992 |
| EP | 879610 | 8/1992 |
| EP | 608343 | 4/1993 |
| EP | 554995 A1 | 8/1993 |
| EP | 554996 | 8/1993 |
| EP | 594349 | 4/1994 |
| EP | 615762 | 9/1994 |
| EP | 513128 | 7/1995 |
| EP | 0673482 | 9/1995 |
| EP | 679440 A1 | 11/1995 |
| EP | 702970 | 3/1996 |
| EP | 897728 | 2/1999 |
| EP | 0937471 | 8/1999 |
| EP | 0937472 | 8/1999 |
| EP | 937476 | 8/1999 |
| EP | 1003581 | 8/1999 |
| EP | 1351732 | 1/2001 |
| EP | 1074273 | 2/2001 |
| EP | 1095668 A1 | 5/2001 |
| EP | 1000631 | 7/2002 |
| EP | 0747391 | 3/2004 |
| EP | 1462134 A1 | 9/2004 |
| EP | 1541185 | 6/2005 |
| EP | 1557163 | 7/2005 |
| EP | 1557189 A1 | 7/2005 |
| EP | 1568389 | 8/2005 |
| EP | 1304129 | 11/2005 |
| EP | 1610848 A1 | 1/2006 |
| EP | 1645301 | 4/2006 |
| EP | 1723977 | 11/2006 |
| EP | 1923083 A1 | 11/2006 |
| EP | 1728529 | 12/2006 |
| EP | 1782853 | 5/2007 |
| EP | 1819382 | 8/2007 |
| EP | 2000161 | 12/2008 |
| FR | 2583291 | 12/1986 |
| FR | 2622457 | 5/1989 |
| FR | 2697434 A1 | 5/1994 |
| FR | 2740345 | 4/1997 |
| FR | 2767479 | 2/1999 |
| FR | 2857654 | 1/2005 |
| GB | 664044 | 1/1952 |
| GB | 2091107 | 7/1982 |
| GB | 2229497 | 9/1990 |
| GB | 2153445 | 8/1995 |
| GB | 2309644 | 8/1997 |
| GB | 0007071.4 | 3/2000 |
| IN | 165367 | 3/1986 |
| JP | 56-163486 | 12/1981 |
| JP | 57-000033 | 1/1982 |
| JP | 64-035671 U | 3/1989 |
| JP | 01-100495 | 4/1989 |
| JP | 02-126184 | 5/1990 |
| JP | 02-182267 | 7/1990 |
| JP | 4-224764 A | 8/1992 |
| JP | 4-507059 | 12/1992 |
| JP | 05-337179 | 12/1993 |
| JP | 06-055644 | 1/1994 |
| JP | 06-034825 | 10/1994 |
| JP | 06-296691 | 10/1994 |
| JP | H07-500039 | 1/1995 |
| JP | 7-502678 | 3/1995 |
| JP | 09166474 | 6/1997 |
| JP | 3017167 | 11/1999 |
| JP | 2000237308 A | 9/2000 |
| JP | 2003284777 | 10/2003 |
| JP | 2004-503303 | 2/2004 |
| JP | 2004-516895 | 6/2004 |
| JP | 2006250582 | 9/2006 |
| JP | 2007-509662 | 4/2007 |
| RU | 2111019 | 5/1997 |
| RU | 2091087 | 9/1997 |
| RU | 2212254 | 9/2003 |
| WO | 8502256 | 5/1985 |
| WO | 8702895 A1 | 5/1987 |
| WO | 8907463 | 8/1989 |
| WO | 90/09202 | 8/1990 |
| WO | 9110460 | 7/1991 |
| WO | 9110677 | 7/1991 |
| WO | 91/14467 A1 | 10/1991 |
| WO | 9301573 | 1/1993 |
| WO | 9303780 | 3/1993 |
| WO | 9307922 A1 | 4/1993 |
| WO | 9412228 | 6/1994 |
| WO | 94/26331 A1 | 11/1994 |
| WO | 9524233 | 9/1995 |
| WO | 96/07443 A1 | 3/1996 |
| WO | 9626754 | 9/1996 |
| WO | 96/32973 | 10/1996 |
| WO | 9638190 | 12/1996 |
| WO | 9707841 | 3/1997 |
| WO | 9710865 A1 | 3/1997 |
| WO | 9730742 | 8/1997 |
| WO | 9734919 | 9/1997 |
| WO | 9736626 | 10/1997 |
| WO | 9810813 | 3/1998 |
| WO | 9856436 | 12/1998 |
| WO | 9857688 | 12/1998 |
| WO | 9907425 | 2/1999 |
| WO | 9915214 | 4/1999 |
| WO | 9916487 | 4/1999 |
| WO | 9921598 | 5/1999 |
| WO | 9938554 | 8/1999 |
| WO | 9948546 | 9/1999 |
| WO | 9965548 A1 | 12/1999 |
| WO | 0037129 | 6/2000 |
| WO | 00/51668 | 9/2000 |
| WO | 01/19434 A1 | 3/2001 |
| WO | 0126710 | 4/2001 |
| WO | 01/30425 | 5/2001 |
| WO | 0172361 | 10/2001 |
| WO | 0195959 A1 | 12/2001 |
| WO | 0205876 | 1/2002 |
| WO | 0224257 | 3/2002 |
| WO | 02/053214 | 7/2002 |
| WO | 02064196 | 8/2002 |
| WO | 02/076535 | 10/2002 |
| WO | 02/076537 | 10/2002 |
| WO | 02/092153 | 11/2002 |
| WO | 02076536 | 12/2002 |
| WO | 03057283 | 7/2003 |
| WO | 03063680 | 8/2003 |
| WO | 9733638 | 9/2003 |
| WO | 03080160 | 10/2003 |
| WO | 03099357 | 12/2003 |
| WO | 2004/002556 A1 | 1/2004 |
| WO | 2004004825 | 1/2004 |
| WO | 2004007002 A1 | 1/2004 |
| WO | 2004/024218 | 3/2004 |
| WO | 2004035113 A2 | 4/2004 |
| WO | 2004069314 | 8/2004 |
| WO | 2004/078240 | 9/2004 |
| WO | 2004/078242 A2 | 9/2004 |
| WO | 2004078239 A1 | 9/2004 |
| WO | 2004078241 | 9/2004 |
| WO | 2004080306 | 9/2004 |
| WO | 2004084795 | 10/2004 |
| WO | 2004095379 | 11/2004 |
| WO | 2005018721 | 3/2005 |
| WO | 2005037352 | 4/2005 |
| WO | 2005/046770 | 5/2005 |
| WO | 2005089835 | 9/2005 |
| WO | 2005097233 A2 | 10/2005 |

(56) References Cited

FOREIGN PATENT DOCUMENTS

| | | |
|---|---|---|
| WO | 2005097240 A1 | 10/2005 |
| WO | 2006039930 A1 | 4/2006 |
| WO | 2006/045529 | 5/2006 |
| WO | 2006045425 | 5/2006 |
| WO | 2006045525 | 5/2006 |
| WO | 20061045528 | 5/2006 |
| WO | 2006/058883 | 6/2006 |
| WO | 2006/069454 | 7/2006 |
| WO | 2006076921 | 7/2006 |
| WO | 2006116997 | 11/2006 |
| WO | 2006/128794 | 12/2006 |
| WO | 2007/030957 | 3/2007 |
| WO | 2007041843 | 4/2007 |
| WO | 2007/107559 | 9/2007 |
| WO | 2007107558 A2 | 9/2007 |
| WO | 2007107561 | 9/2007 |
| WO | 2007/134954 | 11/2007 |
| WO | 2008/037801 | 4/2008 |
| WO | 2008057223 | 5/2008 |

OTHER PUBLICATIONS

Chia Kai Su et al, Process Biochemistry, 2006, vol. 41, Part 2, pp. 257-263.

Dennison, Clive et al, Protein Expression and Purification, 1997, vol. 11, Part 2, pp. 149-161.

Fransson et al, Pharmaceutical Research, 1997, vol. 14, Part 5, pp. 606-612.

Leonil et al, Enzyme and Microbiol Technology, 1994, vol. 16, Part 7, pp. 591-595.

Paule, B.J.A. et al, Protein Expression and Purification, 2004, vol. 34, Part 2, pp. 311-316.

Annersten, M. et al., Insulin Pens Dribble From the Tip of the Needle After Injection, Practical Diabetes Int., vol. 17(4), pp. 109-111 (2000).

Beckmann, Sensors, Memory, Circuits, Polyapply Newsletter, vol. 1(3), (2006).

Gnanalingham, M.G. et al., Accuracy and Reproducibility of Low Dose Insulin Administration Using Pen-Injectors and Syringes, Downloaded From ADC.BMJ.Com on Jan. 9, 2008.

GEARING MECHANISM FOR AN INJECTION DEVICE

CROSS-REFERENCE TO RELATED APPLICATIONS

This application is a continuation of U.S. application Ser. No. 12/300,540 (Issue Fee Pending) filed Feb. 26, 2009, which is a 35 U.S.C. §371 national stage application of International Patent Application PCT/EP2007/054796 (published as WO 2007/132019), filed May 16, 2007, which claimed priority of Danish Patent Application PA 2006 00690, filed May 16, 2006; this application further claims priority under 35 U.S.C. §119 of U.S. Provisional Application 60/813,895, filed Jun. 15, 2006; the contents of all above-named applications are incorporated herein by reference.

FIELD OF THE INVENTION

The present invention relates to a gear mechanism for an injection device, the gear mechanism comprising a lever mechanism for obtaining a gearing. In particular the present invention relates to a gear mechanism comprising a plurality of pivotally connected members.

BACKGROUND OF THE INVENTION

Syringe devices comprising a gear mechanism are known in the art and examples may be seen in WO 01/95959 and WO 03/080160. WO 01/95959 discloses an injection device for injection of set doses of medicine from a cartridge. The syringe device comprises a gearbox which provides a gearing between an axial movement of an injection button and a nut engaging a piston rod relative to a housing. A gear wheel transmission is established between the nut and the injection button.

It is an object of the present invention to provide a gearing mechanism which is more simple than prior art gear mechanisms. A further object of the invention is to provide a gear mechanism which enables a wider range of obtainable gear ratios as compared to prior art gear mechanisms.

BRIEF DESCRIPTION OF THE INVENTION

In a first aspect of the invention, the invention relates to an injection device for accommodation of a reservoir comprising a piston movable within the reservoir and a medicament to be injected, the injection device comprising:
- a base member;
- a plunger for driving the piston in a distal direction;
- a driving member movable in a proximal direction relative to an initial position so as to set a dose and movable in a distal direction towards the initial position so as to eject a dose of the medicament; and
- a gear mechanism providing a gearing between the driving member and the plunger such that when the driving member is moved at a first speed relative to the base member, the plunger is moved at a second speed relative to the base member;

wherein the gear mechanism comprises a lever mechanism coupling a distally directed movement of the driving member with a distally directed movement of the plunger.

In one embodiment, the gearing mechanism may be so arranged that at least two of the base member, the plunger and the driving member are pivotally connected to the gear mechanism.

In another embodiment, the gearing mechanism may be so arranged that both the base member, the plunger and the driving member are pivotally connected to the gear mechanism.

The injection device may be provided as a pen-injector for manually administering set doses of a medicament, where the piston of a reservoir accommodated in the device is axially moveable upon axially movement of the driving member. The driving member is axially movable in the distal direction responsive to a distally directed push-force exerted by the hand of a user. The push-force may be applied directly on the driving member or via one or more intermediate members.

The medicament containing reservoir may form an integral part of the injection device such that an emptied reservoir cannot be replaced, whereby a user will dispose off the injection device when the reservoir has been emptied. Alternatively, the device may allow replacement of a used reservoir by a new reservoir or allow the user to change between reservoirs containing different kinds of medication and/or the same type of medication at different concentrations.

The plunger and the piston of the reservoir may be interconnected by a piston rod, which may be locked for movement in the proximal direction such that when the plunger is moved in the proximal direction during dose setting, the piston rod remains in essentially the same position relative to the plunger. Moreover, the plunger may be adapted to move the piston rod in the distal direction during dose ejection, whereby a medicament contained in the reservoir is expelled.

Alternatively, the piston rod is adapted to retract a fixed distance in a proximal direction during an initial phase of a dose setting procedure, and adapted to move in a distal direction as a dose is being set.

The gear mechanism provides a gearing between the driving member and the plunger such that when the driving member is moved at a first speed relative to the base member, the plunger is moved at a second speed relative to the base member. Accordingly it will be appreciated, that when the driving member is moved a first distance, the plunger is moved a second distance.

In another embodiment the second speed is lower than the first speed, whereby the second distance is shorter than the first distance. This provides the advantage that the gear mechanism converts a relatively low force applied to the driving member to a relatively high force applied to the plunger.

In a further embodiment, the second speed is higher than the first speed, whereby the second distance is longer than the first distance.

The gear mechanism may comprise a first, second and third connecting member each of which is exclusively connected to one of the base member, the plunger and the driving member. In the context of the present invention the term "exclusively connected" shall be understood such that each of the first, second and third connecting member is directly connected to only one of the base member, the plunger and the driving member, but may be indirectly connected i.e. via one or more elements, to the another of the three elements. As an example, the first connecting member may be directly connected to the base member and indirectly connected to the driving member via the second connecting member.

The connecting members of the gear mechanism each operate in a corresponding plane, e.g. the first connecting member is adapted to rotate in a first plane perpendicular to a rotational axis of said first connecting member.

In one embodiment the three planes are spaced apart and do not coincide. This provides a gear mechanism wherein none of the connecting members limits the rotational movement of another connecting member. In another embodiment, two of said three planes coincide, whereby a compact configuration may be provided. However, as two of the connecting members operate in the same plane, each of said two connecting members is limited in its rotational movement by the other of the two connecting members.

In one embodiment the first connecting member is pivotally and directly connected to the base member, the second connecting member is pivotally and directly connected to the driving member, and the third connecting member is pivotally and directly connected to the plunger. Furthermore, at least one of the second and third connecting members is pivotally connected to the first connecting member.

As an example the first connecting member may be pivotally connected to the base member by means of a first pivotal connection, the second member may be pivotally connected to the first member by means of a second pivotal connection, and the third member may be pivotally connected to the first member by means of a third pivotal connection. As the each of the second and third connecting members may also be connected to one of plunger and the driving member, movement of the base member, the plunger and the driving member are interdependent.

In one embodiment the distance from the third pivotal connection to each of the first and the second pivotal connections is shorter than the distance between the first and the second pivotal connections.

By providing the first, the second and third pivotal connections on the first connecting member, said member serves as a moment arm. Thus, if the first connecting member is allowed to rotate about the first pivotal connection, a force applied to the second pivotal connection results in an even larger force acting on the third pivotal connection. Hence, if the distance between the third pivotal connection and each of the first and second pivotal connections is identical, a force of 1 Newton applied to the second pivotal connection results in a force of 2 Newton applied to the third pivotal connection.

From the above it will be appreciated, that the position of the third pivotal connection is decisive for the gearing of the injection device. Hence, in one embodiment the third pivotal connection is provided closer to the first pivotal connection than to the second pivotal connection, and in another embodiment the third pivotal connection is provided closer to the second pivotal connection than to the first pivotal connection.

It will be appreciated, that the relationship between the distance from the first pivotal connection and each of the second and third pivotal connections, corresponds to the gearing of the device. Hence, if the distance from the first pivotal connection to the second pivotal connection is three times the distance from the first pivotal connection to the third pivotal connection, a force of 1 Newton applied to the second pivotal connection results in a force of 3 Newton acting on the third pivotal connection.

In one embodiment the first, second and third connecting members have identical lengths. Alternatively, at least one of the second and the third connecting member may be at least 20 percent longer than the first connecting member, such as 50 percent longer, such as 100 percent, such as 150 percent. It will be appreciated, that the longer the second and third connecting member are relative to the first connecting member, the more linear the gear mechanism is.

In some embodiments the second and third connecting members have identical lengths. However it will be appreciated, that the non-linear properties of the gear mechanism may in some embodiments be reduced by providing the second and third connecting members at different lengths. As an example the difference in the length of the second and the third connecting member may be at least 20 percent, such as at least 50 percent, such as at least 100 percent, such as at least 150 percent.

In one special embodiment the gear mechanism comprises a first connecting member pivotally connected to at least two of the base member, the plunger and the driving member such as to each of the of said three elements. This provides a simplified solution comprising only one connecting member. The first connecting member may be arranged to interconnect both the base member, the plunger and the driving member, the latter three members each being pivotally connected to the first connecting member at respective specific locations along the extension of the first connecting member.

Moreover, at least one of the pivotal connections may be adapted to move along the first connecting member, e.g. by providing a groove in the first connecting member in which the pivotal connection is allowed to move. Thus, rotation of the first connecting member about one of the three pivotal connections does not force the slidable pivotal connection to follow an arc-shaped path. Thereby a mechanism is provided wherein each of the base member, the plunger and the driving member is moveable along respective rectilinear paths, the paths being mutually parallel. When the rotatable part of the base member, the plunger and the driving member are forced to rotate around the longitudinal axis of the device, their mutual spacing in directions normal to the longitudinal axis remains fixed.

Furthermore, the base member may comprise a fixed part and a rotatable part, the fixed part being rotationally and translationally retained in relation to a housing of the device, the rotatable part being adapted to rotate relative to the base member about a longitudinal axis of the base member, the rotatable part furthermore being translationally retained in relation to the fixed part.

In a still further embodiment, the driving member is rotatably mounted with respect to the fixed part of the base member, and hence, rotatably mounted relative to a housing of the device. The driving member may be adapted to be lifted in the proximal direction of the device as a function of its rotation, such as provided by a threaded coupling. In such an embodiment, the driving member is moved axially in the proximal direction in accordance with the size of the dose being set by rotating the driving member with respect to the housing.

Moreover, a clutch may be provided between the driving member and the fixed part, said clutch may be adapted to be changed between:
  a coupled position wherein a threaded inner surface of the clutch engages a threaded outer surface of the fixed part such that when the driving member is rotated, the threaded engagement causes the driving member to be moved in a proximal direction, and
  a decoupled position wherein the threaded inner surface of the clutch disengages the threaded outer surface of the fixed part, so as to allow translational and non-rotational movement between the driving member and fixed part.

In a still further embodiment, the driving member, and optionally, the plunger, is/are adapted to also rotate during their translational movement during injection.

DETAILED DESCRIPTION OF THE INVENTION

Figure 2:
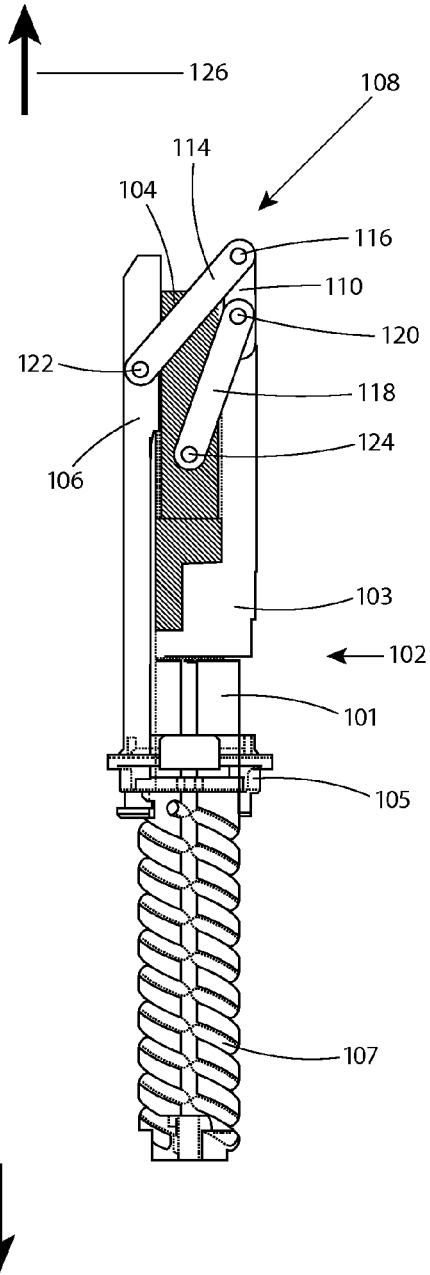
Figure 3:
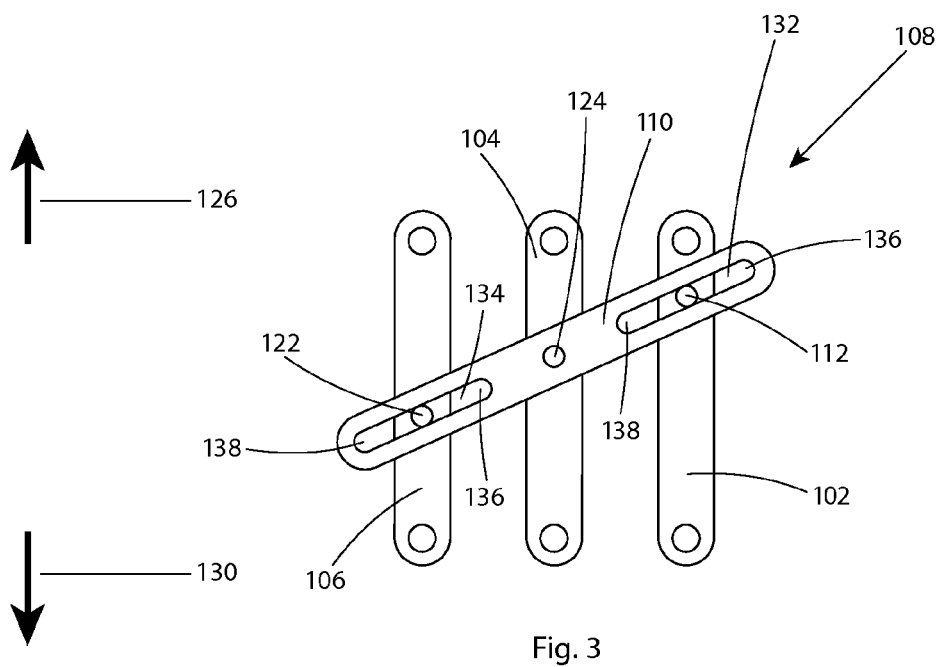
Figure 4:
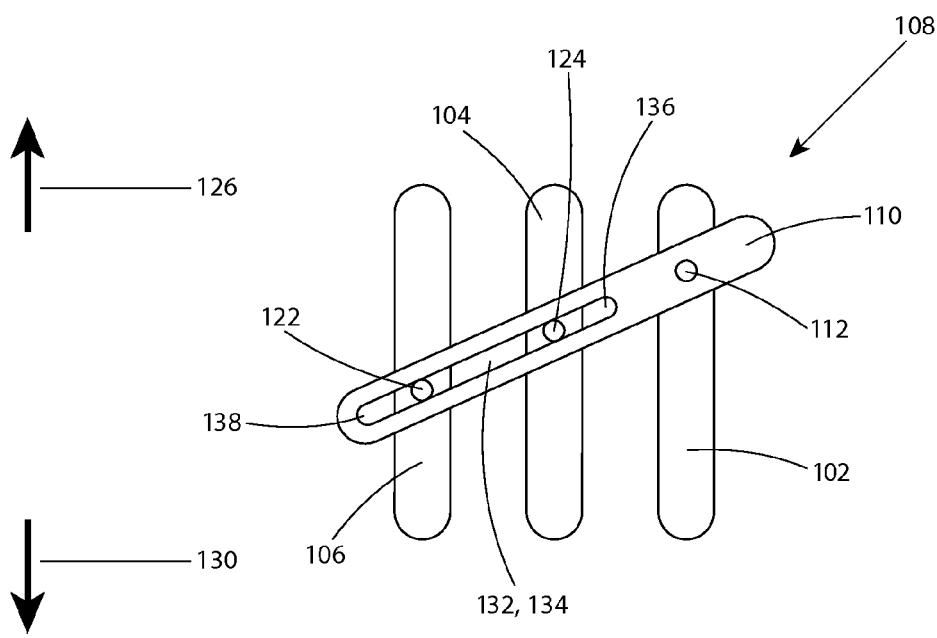

FIGS. 1 and 2 disclose two extreme positions of a first embodiment of the gear mechanism according to the invention, FIG. 3 discloses a second embodiment of the gear mechanism, and FIG. 4 discloses a third embodiment of the gear mechanism.

FIGS. 1 and 2 disclose a dosing assembly 100 for a syringe device, such as a pen based injector. The dosing assembly 100 described below is configured for inclusion in an injection pen having a dosing scheme of the kind disclosed in WO 01/95959, this reference hereby being incorporated by reference. The gear mechanism 108 described below substitutes the tooth and rack based gear-box arrangement of the embodiments shown in the figures of WO 01/95959.

FIGS. 1 and 2 disclose two extreme positions of the gear mechanism. FIG. 1 illustrates the dosing assembly 100 in its initial position wherein no dose is set, and FIG. 2 illustrates the dosing assembly 100 when a maximum dose has been set.

The dosing assembly comprises a base member 102, a plunger 104 and a driving member 106. The plunger 104 and the driving member 106 are movable in an axial direction relative to the base member 102. Moreover, the distance between the base member 102, the plunger 104 and the driving member 106, remains essentially constant during dose setting and ejection of a dose. The base member comprises a fixed part 101 and a rotatable part 103.

The plunger 104 and the driving member 106 are pivotally connected to the base member 102 via a gear mechanism 108. The gear mechanism 108 comprises a first connecting member 110, which in a first end is pivotally connected to the base member 102 by means of a first pivotal connection 112 and in a second end is pivotally connected to a second connecting member 114 via a second pivotal connection 116. Moreover, the first connecting member 110 is pivotally connected to a third connecting member 118 via a third pivotal connection 120. Furthermore, the second connecting member 114 is pivotally connected to the driving member 106 via a fourth pivotal connection 122, and the third connecting member 118, is pivotally connected to the plunger 104 via a fifth pivotal connection 124.

The fixed part 101 is retained rotationally and translationally in relation to a housing of the device. Furthermore, the rotatable part 103 is adapted to be rotated about its longitudinal axis, while being retained translationally in relation to the fixed part 101. Moreover, a clutch 105 of the driving member is adapted to be changed between a coupled position wherein it engages a threaded outer surface 107 of the fixed part 101, and a decoupled position wherein it does not engage the threaded outer surface 107. When the clutch is in its decoupled position the driving member 106 is allowed to move in the distal direction 130 without rotating, as the clutch is disengaged from the threaded outer surface 107.

In order to set a dose, the driving member 106 is rotated about the longitudinal axis of the device. The rotational movement causes the driving member 106 to be moved in the proximal direction due to the engagement between the clutch 105 and the threaded outer surface 107.

As the second connecting member 114 is pivotally connected to the driving member 106, the proximal movement of the driving member 106 causes the first connecting member 110 to rotate about the first pivotal connection 112, as indicated by arrow 128. Due to the rotation, the third connecting member 118 is also forced in the proximal direction 126. As the third pivotal connection 120 is located closer to the first pivotal connection 112 than the second pivotal connection 116, the plunger 104 is moved at a slower speed relative to the base member 102 than the driving member 106. It will be appreciated that the closer the third pivotal connection 120 is to the first pivotal connection 112, the slower the speed of the plunger 104 is relative to the speed of the driving member 106.

In one embodiment the plunger 104 comprises a threaded inner surface (not shown) which is adapted to engage a threaded outer surface of the piston rod (not shown). Moreover, rotational and translational movement of the driving member 106 during dose setting causes rotational and translational movement of the plunger 104. However as described in the aforementioned, the plunger 104 is moved at a slower translational speed, and, thus, in order to maintain the piston rod in substantially the same position during dose setting, the pitch of the thread of the piston rod must be decreased correspondingly relative to the pitch of the threaded outer surface 107.

Alternatively, the plunger 104 is arranged to cooperate with a pawl and ratchet mechanism (not shown) which provides for telescopically engagement between the plunger 104 and the piston.

In an embodiment, a dose setting drum (not shown) is operationally coupled to the driving member 106 for rotating the driving member 106 during dose setting. Additionally, an injection button (not shown) axially extending from the proximal end of the injection device is operationally coupled to the driving member 106 for axially moving the driving member 106 upon manually pushing of the injection button in the distal direction. Said dose setting drum and injection button may be provided as mutually separate members or alternatively, these elements form one unitary member.

FIG. 2 illustrates a situation wherein a dose is set and the device is ready for ejection of a dose. In order to eject a dose, the clutch is changed to its decoupled position, whereby the driving member is allowed to move in the distal direction without rotating, as the clutch does not engage the threaded outer surface. The plunger 104 cooperates with a piston rod (not shown) such that when the plunger is moved in the distal direction 130, the piston rod forces a piston (not shown) in a distal direction whereby a medicament contained in a reservoir (not shown) is expelled.

It will be appreciated that by using the driving member 106 to eject the medicament, the first connecting member 110 serves as a moment arm whereby a relatively small force need be applied to cause the plunger to move in the distal direction 130. Again it will be appreciated, that the closer the third pivotal connection 120 is to the first pivotal connection 112, the smaller a force need be applied to the driving member 106 in order to move the plunger 104. Moreover it will be appreciated, that due to the different speeds, the plunge 104 is moved a shorter distance relative to the base member than the driving member 106, for any angular movement of the first connecting member 110 about the first pivotal connection.

Additionally, it will be appreciated that the gearing between the plunger 104 and the driving member 106 is determined by the length of the first connecting member 110 and the relative position of the first, second, and third pivotal connection 112,116,120 on said first connecting member 110.

FIGS. 3 and 4 disclose a second and third embodiment of the gear mechanism 108. The two embodiments comprise a plunger 104 and a driving member 106 which are movable relative to a base member 102.

The gear mechanism 108 comprises a first connecting member 110, which is pivotally connected to the base member 102, the plunger 104 and the driving member 106, via a first pivotal connection 112, a fifth pivotal connection 124, and a fourth pivotal connection 122, respectively.

In FIG. 3, the first connecting member 110 comprises a first and second groove 132, 134 allowing the first pivotal connection 112 and the fourth pivotal connection 122 to move in a longitudinal direction of the first connecting member 110 between a first and second position 136,138. The fifth pivotal connection 124 is locked for longitudinal movement relative to the longitudinal direction of the first connecting member 110. All three pivotal connections allow the first connecting member 110 to rotate about each of the pivotal connections 112,122,124, such that the first connecting member 110 may pivot relative to the base member 102, the plunger 104 and the driving member 106.

In one embodiment the mutual distance between the base member 102, the plunger 104 and the driving member 106, in directions normal to the longitudinal axis, remains essentially constant during dose setting and ejection of a dose. Accordingly, it will be appreciated that when the driving member 106 is moved in the proximal direction 126, the fourth pivotal connection 122 is moved in the direction of the first position 136, until the first connecting member 110 is at right angle to the plunger 104. Upon further proximal movement of the driving member 106, the fourth pivotal connection 122 is moved away from the first position 136 and towards the second position 138. In order to reduce the friction between the pivotal connections 112,122 and the inner surfaces of the grooves 132,134, said inner surfaces may have a smooth surface with a low coefficient of friction. Alternatively, or as a supplement, bearings may be provided on the pivotal connections 112,122. In yet another alternative, the pivotal connections and the grooves are lubricated so as to reduce the friction between the engaging surfaces.

In FIG. 4 the grooves 132,134 are merged such that two pivotal connections 122,124 are allowed to move in the longitudinal direction of the first connecting member 110, whereas the first pivotal connection 112 is locked for longitudinal movement relative to the first connecting member 110. It will be appreciated that in some embodiments the grooves 132,134 need not be merged in order to enable the gear mechanism to work.

It will be appreciated, that most of the description of the gear mechanism of FIG. 3 also applies to the gear mechanism of FIG. 4.

While the dosing assembly according to the above embodiments have been described with reference to the general dosing scheme of WO 01/95959, it should be stressed that the present invention is not limited to this particular dosing scheme. The gearing arrangement according to the present invention is further adoptable in pen-injectors having various kinds of dosing schemes, such as the ones described in WO9938554, WO2006114395, WO2006114396, US20040215152, U.S. Pat. No. 5,584,815 and U.S. Pat. No. 4,883,472, however, this list being non-exhaustive.

The invention claimed is:

1. A pen-injector for manually administering set doses of a medicament, the injector adapted for accommodating a reservoir comprising a piston movable along a first axis within the reservoir and a medicament to be injected, the pen-injector comprising:
    a base member;
    a plunger for driving the piston axially in a distal direction;
    a driving member axially movable relative to the base member, the driving member movable in a proximal direction relative to an initial position so as to set a dose and manually pushable in a distal direction towards the initial position so as to eject a dose of the medicament; and
    a gear mechanism providing a gearing between the driving member and the plunger such that when the driving member is moved at a first speed relative to the base member, the plunger is moved at a second speed relative to the base member;
    wherein at least two of the base member, the plunger and the driving member are pivotally connected to the gear mechanism, and
    wherein the gear mechanism comprises a lever mechanism coupling a distally directed movement of the driving member with a distally directed movement of the plunger.

2. A pen-injector according to claim 1, wherein the gear mechanism comprises a first connecting member pivotally connected to at least two of the base member, the plunger and the driving member.

3. A pen-injector according to claim 2, wherein the first connecting member is pivotally connected to the base member, the plunger and the driving member.

4. A pen-injector according to claim 1, wherein the gear mechanism comprises a first, second and third connecting member each of which is exclusively connected to one of the base member, the plunger and the driving member.

5. An pen-injector according to claim 4, wherein the second speed is lower than the first speed.

6. A pen-injector according to claim 4, wherein at least one of the second and the third connecting member is at least 20 percent longer than the first connecting member.

7. A pen-injector according to claim 6, wherein at least one of the second and the third connecting member is 50 percent longer than the first connecting member.

8. A pen-injector according to claim 4, wherein the difference in the length of the second and the third connecting member is at least 20 percent.

9. A pen-injector according to claim 8, wherein the difference in the length of the second and the third connecting member is 50 percent.

10. A pen-injector according to claim 4, wherein the base member comprises a fixed part and a rotatable part, the fixed part being rotationally and translationally retained in relation to a housing of the device, the rotatable part being adapted to rotate relative to the base member about a longitudinal axis of the base member, the rotatable part furthermore being translationally retained in relation to the fixed part.

11. A pen-injector according to claim 10, further comprising a clutch provided between the driving member and the fixed part, said clutch being adapted to be changed between:
    a coupled position wherein a threaded inner surface of the clutch engages a threaded outer surface of the fixed part such that when the driving member is rotated, the threaded engagement causes the driving member to be moved in a proximal direction, and
    a decoupled position wherein the threaded inner surface of the clutch disengages the threaded outer surface of the fixed part, so as to allow translational and non-rotational movement between the driving member and fixed part.

12. A pen-injector according to claim 4, wherein the first connecting member is pivotally connected to the base member, the second connecting member is pivotally connected to the driving member, and the third connecting member is pivotally connected to the plunger, and wherein at least one of the second and third connecting members is pivotally connected to the first connecting member.

13. A pen-injector according to claim 12, wherein the first connecting member is pivotally connected to the base member by means of a first pivotal connection, the second member is pivotally connected to the first member by means of a second pivotal connection, and the third member is pivotally connected to the first member by means of a third pivotal connection.

14. A pen-injector according to claim 13, wherein the distance from the third pivotal connection to each of the first and the second pivotal connections is shorter than the distance between the first and the second pivotal connection.

15. A pen-injector according to claim 14, wherein the distance between the third pivotal connection and the first pivotal connection is shorter than the distance between the third pivotal connection and the second pivotal connection.

16. A pen-injector according to claim 14, wherein the distance between the third pivotal connection and the first pivotal connection is longer than the distance between the third pivotal connection and the second pivotal connection.

17. A pen-injector for manually administering set doses of a medicament, the injector adapted for accommodating a reservoir comprising a piston movable along a first axis within the reservoir and a medicament to be injected, the pen-injector comprising:

a base member;

a plunger for driving the piston axially in a distal direction wherein said plunger comprises a threaded inner surface which is adapted to engage a threaded outer surface of a piston rod, or where said plunger is arranged to cooperate with a pawl and ratchet mechanism which provides for telescopic engagement between said plunger and said piston;

a driving member axially movable relative to the base member, the driving member movable in a proximal direction relative to an initial position so as to set a dose and manually pushable in a distal direction towards the initial position so as to eject a dose of the medicament; and a gear mechanism providing a gearing between the driving member and the plunger such that when the driving member is moved at a first speed relative to the base member, the plunger is moved at a second speed relative to the base member;

wherein at least two of the base member, the plunger and the driving member are pivotally connected to the gear mechanism, and wherein the gear mechanism comprises a lever mechanism coupling a distally directed movement of the driving member with a distally directed movement of the plunger.

* * * * *